US00PP25545P2

(12) United States Plant Patent
Fischer-Toehl

(10) Patent No.: US PP25,545 P2
(45) Date of Patent: May 12, 2015

(54) GERANIUM PLANT NAMED 'TOSFORICE'

(50) Latin Name: *Pelargonium peltatum*
Varietal Denomination: Tosforice

(71) Applicant: Ball Horticultural Company, West Chicago, IL (US)

(72) Inventor: Ilse Fischer-Toehl, Kirchlinteln (DE)

(73) Assignee: Ball Horticultural Company, West Chicago, IL (US)

( * ) Notice: Subject to any disclaimer, the term of this patent is extended or adjusted under 35 U.S.C. 154(b) by 79 days.

(21) Appl. No.: 13/998,054

(22) Filed: Sep. 26, 2013

(51) Int. Cl.
*A01H 5/02* (2006.01)

(52) U.S. Cl.
USPC ..... Plt./332

(58) Field of Classification Search
CPC ..... A01H 5/0277; A01H 5/02; A01H 5/00
USPC ..... Plt./332
See application file for complete search history.

*Primary Examiner* — Kent L Bell
(74) *Attorney, Agent, or Firm* — Audrey Charles

(57) ABSTRACT

A new and distinct cultivar of Ivy Geranium plant named 'Tosforice', characterized by its double type, red and white bicolored flowers, dark green-colored foliage, moderate growth vigor, and compact, mounded-spreading growth habit, is disclosed.

1 Drawing Sheet

Latin name of genus and species of plant claimed: *Pelargonium peltatum.*

Variety denomination: 'Tosforice'.

BACKGROUND OF THE INVENTION

The present invention relates to a new and distinct cultivar of Ivy Geranium plant botanically known as *Pelargonium peltatum* and hereinafter referred to by the cultivar name 'Tosforice'.

The new cultivar originated in a controlled breeding program in Weener-Halte, Germany during August 2007. The objective of the breeding program was the development of Ivy Geranium cultivars that flower uniformly and have dark green-colored foliage, and a compact, mounded-spreading growth habit.

The new Ivy Geranium cultivar 'Tosforice' was produced by grafting the *Pelargonium peltatum* plant 'Mexikanerin', not patented, which contains a unique viroid that causes dichroism, with the proprietary *Pelargonium peltatum* breeding selection coded N 540, not patented. 'Mexikanerin' was the rootstock and breeding selection N 540 was the scion. Breeding selection N 540 is characterized by its double-type, bright red flowers, dark green-colored foliage having very dark zonation, moderate growth vigor, and mounded-spreading growth habit. After the grafting method, terminal cuttings were taken and propagated. The viroid of 'Mexikanerin' passed to the grafting and yielded a new phenotype of red and white bicolor flowers. There was variation among the plants and selections were made based on flower color. A single plant selection was subsequently chosen for further evaluation and for asexual propagation via vegetative cuttings. While the mechanism of the viroid is not known, the new trait of dichroism is stable and heritable in that it is passed on to future generations through asexual propagation without the rootstock.

Asexual reproduction of the new cultivar by terminal stem cuttings since Spring 2008 in Weener-Halte, Germany and Arroyo Grande, Calif. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Tosforice' as a new and distinct cultivar of Ivy Geranium plant:

1. Double-type, red and white bicolored flowers;
2. Dark green-colored foliage;
3. Moderate growth vigor; and
4. Compact, mounded-spreading growth habit.

Plants of the new cultivar differ from plants of the rootstock 'Mexikanerin' primarily in flower color and foliage color. Plants of the new cultivar differ from plants of the scion N 540 parent primarily in flower color.

Of the many commercially available Ivy Geranium cultivars, the most similar in comparison to the new cultivar is 'Meriblue', U.S. Plant Pat. No. 10,266. However, in side by side comparisons, plants of the new cultivar differ from plants of 'Meriblue' in at least the following characteristics:

1. Plants of the new cultivar have a flower color different from plants of 'Meriblue'; and
2. Plants of the new cultivar have larger leaves than plants of 'Meriblue'.

In addition, the new cultivar is similar in comparison to Precision Burgundy Ice 'Balcolbure', not patented. However, in comparison, plants of the new cultivar differ from plants of 'Balcolbure' in at least the following characteristics:

1. Plants of the new cultivar have a more compact habit than plants of 'Balcolbure'; and
2. Plants of the new cultivar have a slightly different flower color than plants of 'Balcolbure'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Tosforice'. The plants were grown in 4.5-inch pots for 9 weeks in a greenhouse in West Chicago, Ill.

DETAILED BOTANICAL DESCRIPTION

Figure 1:
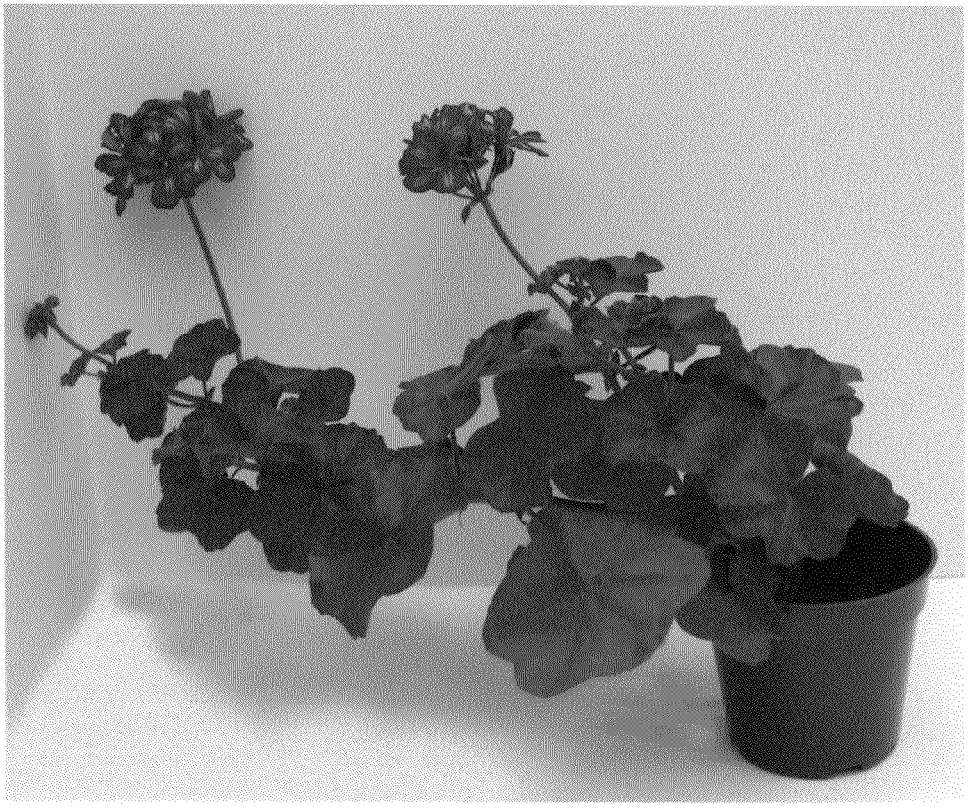
FIG. 1 illustrates a side view of the overall growth and flowering habit of 'Tosforice'.
Figure 2:
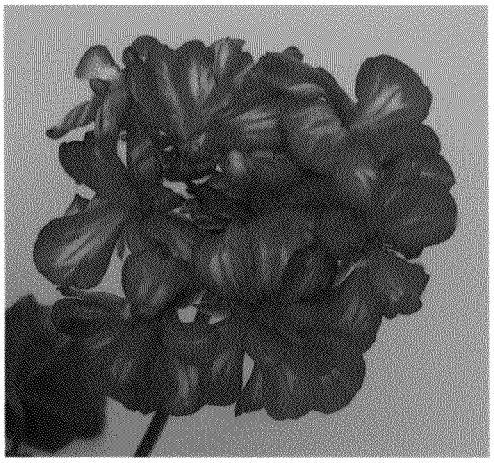
FIG. 2 illustrates a close-up view of an individual umbel of 'Tosforice'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2007 edition, except where general color terms of ordinary significance are used. The color values were determined in May 2013 under natural light conditions in West Chicago, Ill.

The following descriptions and measurements describe plants produced from cuttings from stock plants and grown in a glass-covered greenhouse under conditions comparable to those used in commercial practice. The plants were grown in West Chicago, Ill. in 4.5-inch pots for 9 weeks utilizing a soilless growth medium. Greenhouse temperatures were maintained at approximately 70° F. to 77° F. (21° C. to 25° C.) during the day and approximately 65° F. to 68° F. (18° C. to 20° C.) during the night. Greenhouse light levels of 2,500 footcandles to 6,000 footcandles were maintained during the day. Measurements and numerical values represent averages of typical plants.

Botanical classification: *Pelargonium peltatum* cultivar Tosforice.

Parentage: 'Tosforice' was produced by grafting the *Pelargonium peltatum* plant 'Mexikanerin', not patented, with the proprietary *Pelargonium peltatum* breeding selection coded N 540, not patented.

Propagation:

*Type cutting*.—Terminal stem.

*Time to initiate roots*.—Approximately 11 to 15 days.

*Time to produce a rooted cutting*.—Approximately 28 to 35 days.

*Root description*.—Fibrous.

*Rooting habit*.—Freely branching.

Plant description:

*Commercial crop time*.—Approximately 8 to 10 weeks from a rooted cutting to finish in a 10 cm pot.

*Growth habit and general appearance*.—Moderately vigorous, mounded, compact-spreading.

*Size*.—Height from soil level to top of plant plane: Approximately 24.5 cm. Width: Approximately 44.0 cm.

*Branching habit*.—Freely basal branching, pinching will increase basal branching. Quantity of main branches per plant: Approximately 2.

*Branch*.—Strength: Moderate. Length: Approximately 26.0 cm. Diameter: Approximately 4.0 mm. Length of central internode: Approximately 3.8 cm. Texture: Densely pubescent with appressed hairs. Color of young stem: 144A. Color of mature stem: 146B with an overlay of 187A.

Foliage description:

*General description*.—Quantity of leaves per lateral branch: Approximately 12. Fragrance: None. Form: Simple. Arrangement: Opposite.

*Leaves*.—Aspect: Petiole is at an acute angle to stem, blade is perpendicular to stem. Shape: Reniform. Margin: Entire, palmately lobed. Apex: Rounded to broadly acute. Base: Cordate. Venation pattern: Palmate. Length of mature leaf: Approximately 6.9 cm. Width of mature leaf: Approximately 7.6 cm. Texture of upper surface: Rugous, densely pubescent. Texture of lower surface: Rugous, moderately pubescent. Color of upper surface of young foliage: 137A with faint zonation of N186A and venation of 146B. Color of lower surface of young foliage: 137B with venation of 146B. Color of upper surface of mature foliage: Closest to but darker than N137A with very faint zonation of N186A and venation of 146B. Color of lower surface of mature foliage: N137D with venation of 146B.

*Petiole*.—Length: Approximately 3.8 cm. Diameter: Approximately 2.0 mm. Texture: Densely pubescent with appressed hairs. Color: 146B, occasionally with an overlay of 187A.

Flowering description:

*Flowering habit*.—'Tosforice' is freely flowering under outdoor growing conditions with substantially continuous blooming from spring through autumn and year-round in greenhouse environment.

*Lastingness of individual flower on the plant*.—Approximately 10 to 13 days.

Inflorescence description:

*General description*.—Type: Hemispherical umbel. Positioned above foliage. Quantity of fully open umbels per plant: Approximately 3. Quantity of developing umbels per plant: Approximately: 2. Fragrance: None. Length or height: Approximately 5.1 cm. Width: Approximately 7.7 cm. Quantity of fully open flowers per inflorescence: Approximately 10.

*Peduncle*.—Strength: Strong. Aspect: Erect. Length: Approximately 11.7 cm. Diameter: Approximately 3.0 mm. Texture: Densely pubescent with appressed hairs. Color: 146B, occasionally with a faint overlay of 187A.

Flower description:

*General description*.—Type: Double.

*Bud*.—Rate of opening: Generally takes 2 to 3 days for bud to progress from first color to fully open flower.

*Bud just before opening*.—Shape: Elliptic. Length: Approximately 1.4 cm. Width: Approximately 7.0 mm. Sepal texture: Densely pubescent. Petal texture: Glabrous. Petal color: 46A.

*Corolla*.—Shape: Round. Diameter: Approximately 4.1 cm. Depth: Approximately 1.7 cm.

*Petals*.—Quantity: Approximately 9 to 10 petals and 1 to 2 irregularly-shaped petaloids per flower. Shape: Obovate. Appearance: Dull. Margin: Entire. Apex: Obtuse. Base: Attenuate. Length of upper petals: Approximately 2.8 cm. Width of upper petals: Approximately 1.6 cm. Length of lower petals: Approximately 2.2 cm. Width of lower petals: Approximately 1.0 to 1.7 cm. Texture of upper and lower surfaces: Glabrous. Color of upper surface of upper petals when fully open: Margins of 46A, centers of NN155D with a heavy overlay of 46A, center of base 61A. Color of lower surface of upper petals when fully open: NN155D with stripes and margins of 46D and venation of 61 A. Color of upper surface of lower petals when fully open: Margins of 46A, centers of NN155D with a heavy overlay of 46A. Color of lower surface of lower petals when fully open: NN155D with stripes and margins of 46D.

*Calyx*.—Shape: Star. Diameter: Approximately 2.5 cm.

*Sepals*.—Quantity per flower: Approximately 5, fused at base. Shape: Lanceolate. Margin: Entire. Apex: Acuminate. Length of upper sepal: Approximately 1.3 cm. Width of upper sepal: Approximately 5.0 mm. Length of lower sepals: Approximately 1.3 cm. Width of lower sepals: Approximately 3.0 mm. Texture of upper surface: Glabrous. Texture of lower surface: Densely pubescent. Color of upper surface: 137C. Color of lower surface: 137B occasionally with an overlay of 187B especially heavy on upper sepal.

*Pedicel*.—Strength: Strong. Aspect: Acute angle to peduncle. Length: Approximately 2.1 cm. Diameter: Approximately 2.0 mm. Texture: Densely pubescent with a mixture of glandular and nonglandular hairs. Gland color: Colorless, transparent. Color: 146B with an overlay of 187B.

*Reproductive organs*.—Androecium: Quantity of mature stamens: Approximately 3 to 5 per flower. Anther shape: Oblong. Anther length: Approximately 3.0 mm. Anther color: N92C. Filament length: Approximately 8.0 mm. Filament color: NN155D with an overlay of N66D. Pollen amount: Sparse. Pollen color: 30C. Gynoecium: Pistil quantity: 1 per flower. Pistil length: Approximately 1.0 cm. Stigma shape: 5-branched. Stigma length: Approximately 3.0 mm. Stigma color: 59A. Style length: Approximately 2.0 mm. Style color: 145D. Ovary length: Approximately 5.0 mm. Ovary texture: Densely pubescent. Ovary color: 143B.

Seed and fruit production: Neither seed nor fruit production has been observed.

Disease and pest resistance: Resistance to pathogens and pests common to Ivy Geranium has not been observed.

What is claimed is:

1. New and distinct cultivar of Ivy Geranium plant named 'Tosforice', substantially as herein illustrated and described.

* * * * *